United States Patent [19]

Buerstinghaus et al.

[11] 4,327,090
[45] Apr. 27, 1982

[54] OXIMINOPHOSPHORIC ACID DERIVATIVES, THEIR PREPARATION AND THEIR USE IN PEST CONTROL

[75] Inventors: Rainer Buerstinghaus, Weinheim-Luetzelsachsen; Karl Kiehs, Lampertheim; Hardo Siegel, Speyer; Heinrich Adolphi, Limburgerhof, all of Fed. Rep. of Germany

[73] Assignee: BASF Aktiengesellschaft, Fed. Rep. of Germany

[21] Appl. No.: 213,790

[22] Filed: Dec. 8, 1980

[30] Foreign Application Priority Data

Dec. 29, 1979 [DE] Fed. Rep. of Germany ....... 2952738

[51] Int. Cl.³ ................. A61K 31/665; C07D 306/09; C07D 307/06
[52] U.S. Cl. ............................ 424/203; 260/345.9 R; 260/347.7; 260/347.2; 260/346.11
[58] Field of Search .................... 260/345.9 R, 346.11, 260/347.2, 347.7; 424/203

[56] References Cited

U.S. PATENT DOCUMENTS

| | | | |
|---|---|---|---|
| 3,639,537 | 2/1972 | Kaufman | 424/203 |
| 4,058,606 | 11/1977 | Kiehs et al. | 260/345.9 R |
| 4,125,542 | 11/1978 | Stach | 260/345.9 R |

FOREIGN PATENT DOCUMENTS

| | | |
|---|---|---|
| 1052981 | 3/1959 | Fed. Rep. of Germany . |
| 1238902 | 4/1967 | Fed. Rep. of Germany . |
| 1545977 | 1/1970 | Fed. Rep. of Germany . |
| 2304848 | 8/1974 | Fed. Rep. of Germany . |
| 798703 | 7/1958 | United Kingdom ............ 424/203 |
| 1072979 | 6/1967 | United Kingdom ............ 424/203 |
| 1091738 | 11/1967 | United Kingdom ............ 424/203 |
| 1417372 | 12/1975 | United Kingdom ............ 424/203 |

*Primary Examiner*—Nicky Chan
*Attorney, Agent, or Firm*—Keil & Witherspoon

[57] ABSTRACT

Oximinophosphoric acid derivatives of the formula I

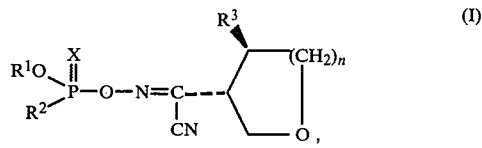

where $R^1$ is unbranched or branched alkyl of up to 4 carbon atoms, $R^2$ is unbranched or branched alkoxy or alkylthio of up to 4 carbon atoms, unbranched or branched alkyl of up to 3 carbon atoms, phenyl, amino or alkylamino or dialkylamino, where each alkyl is unbranched or branched and of up to 4 carbon atoms, $R^3$ is hydrogen or methyl, X is oxygen or sulfur and n is 1 or 2, and their use in pest control.

5 Claims, No Drawings

OXIMINOPHOSPHORIC ACID DERIVATIVES, THEIR PREPARATION AND THEIR USE IN PEST CONTROL

The present invention relates to oximinophosphoric acid derivatives, processes for their preparation, pest control agents which contain these phosphoric acid derivatives as active ingredients, and a method of pest control using these active ingredients.

Oximinophosphoric acid derivatives are known from German Published Applications DAS No. 1,052,981 and DAS No. 1,238,902, and from German Laid-Open Application DOS No. 2,304,848. They may be used for the control of insects and Arachnidae.

We have found that oximinophosphoric acid derivatives of the formula I

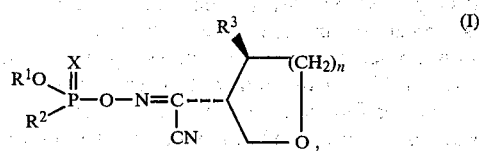

where
R$^1$ is unbranched or branched alkyl of up to 4 carbon atoms,
R$^2$ is unbranched or branched alkoxy or alkylthio of up to 4 carbon atoms, unbranched or branched alkyl of up to 3 carbon atoms, phenyl, amino or alkylamino or dialkylamino, where each alkyl is unbranched or branched and of up to 4 carbon atoms,
R$^3$ is hydrogen or methyl,
X is oxygen or sulfur and
n is 1 or 2,
are very effective insecticides, acaricides and nematicides, superior to the prior art active ingredients of similar structure and/or similar type of action.

Examples of unbranched or branched alkyl R$^1$ are methyl, ethyl, propyl, isopropyl, butyl and isobutyl; examples of unbranched or branched alkyl, alkoxy or alkylthio R$^2$ are methyl, ethyl, n-propyl, isopropyl, methoxy, ethoxy, propoxy, butoxy, methylthio, ethylthio, n-propylthio, isopropylthio, n-butylthio, sec.-butylthio and isobutylthio. Examples of alkylamino and dialkylamino R$^2$ are methylamino, dimethylamino, ethylamino, diethylamino, methylethylamino, n-butylamino and di-n-butylamino.

Preferred substituents at R$^1$ are methyl and ethyl; preferred substituents at R$^2$ are methoxy, ethoxy, methyl, ethyl, phenyl, amino, methylamino, dimethylamino and isopropylamino.

The oximinophosphoric acid derivatives of the formula I may be obtained by reacting an α-oximinonitrile of the formula II, in the presence or absence of an acid acceptor, or by reacting an alkali metal salt, alkaline earth metal salt or unsubstituted or substituted ammonium salt of such an α-oximinonitrile, with a (thiono)(thiol)phosphoric(phosphonic) acid ester(amide) halide of the formula III, in accordance with the following equation:

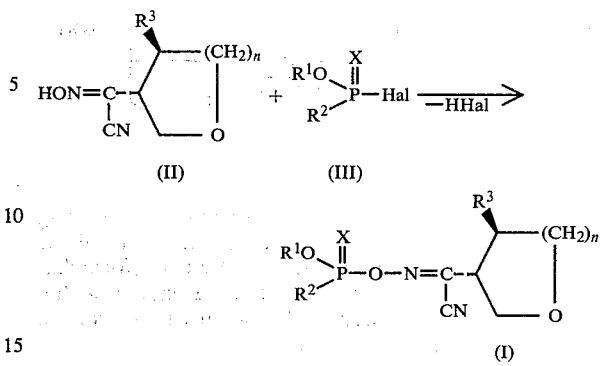

wherein R$^1$, R$^2$, R$^3$ and n have the above meanings and Hal is halogen, preferably chlorine.

The reaction is advantageously carried out in a solvent or diluent which is inert toward the reactants: for example, the following are suitable: aliphatic and aromatic hydrocarbons and chlorohydrocarbons, eg. petroleum ether, benzene, toluene, xylene, gasoline, methylene chloride, chloroform, carbon tetrachloride, 1,2-dichloroethane and chlorobenzene, ethers, e.g. diethyl ether, di-n-butyl ether, methyl tert.-butyl ether, tetrahydrofuran and dioxane, ketones, eg. acetone, methyl ethyl ketone and methyl isopropyl ketone, and nitriles, eg. acetonitrile and propionitrile. Mixtures of these solvents or diluents may also be used.

Suitable acid acceptors are the bases conventionally used in the phosphorylation of hydroxy compounds. Alkali metal carbonates and alcoholates, eg. sodium carbonate, potassium carbonate, sodium methylate and ethylate and potassium methylate and ethylate, have proved particularly suitable, as have aliphatic, aromatic and heterocyclic amines, eg. triethylamine, dimethylamine, piperidine, dimethylaniline, dimethylbenzylamine and pyridine. In some cases, it is advantageous to use alkyl-lithium compounds, eg. n-butyl-lithium.

It is also possible, instead of carrying out the reaction in the presence of an acid acceptor, first to prepare a salt, eg. an alkali metal salt, alkaline earth metal salt or ammonium salt, of the α-oximinonitrile of the formula II, in an undiluted form, and then to react this further with a compound of the formula III.

Usually, the starting materials are employed in the equimolar ratio. An excess of one or other reactant may be advantageous in some cases.

The reaction temperature can be varied within a substantial range. In general, the reaction is carried out from 0° to 120° C., preferably from 20° to 50° C. Since the reaction is, in some cases, exothermic, external cooling at the start of the reaction may be advantageous.

The reaction is usually carried out under atmospheric pressure.

The α-oximinonitriles of the formula II, used as starting materials for the preparation of the compounds I, have not been disclosed previously. However, they may be prepared in a conventional manner (German Published Application DAS No. 1,567,142) by chlorinating a corresponding 3-formyldihydropyran(furan) oxime of the formula IV and then reacting the product with sodium cyanide or potassium cyanide in accordance with the following equation:

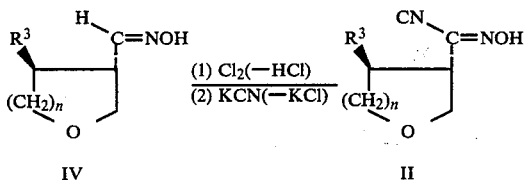

Oximes of the formula IV are obtained by reacting the corresponding 3-formyldihydropyran(furan) of the formula V, which may be prepared by hydroformylating the corresponding olefin in the presence of a rhodium catalyst, with hydroxylamine hydrochloride in accordance with the equation:

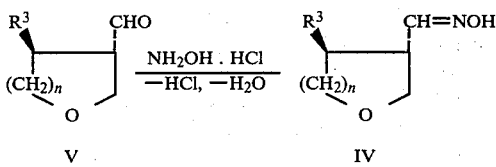

In these equations, $R^3$ has the above meanings and n is 1 or 2.

The (thiono)(thiol)phosphoric(phosphonic) acid ester(amide) halides III additionally required for the synthesis of the compounds of the formula I are known from Houben-Weyl, Methoden der organischen Chemie, Volume XII/2, pages 274 et seq., Georg Thieme-Verlag, Stuttgart, 1964, and may be prepared by the methods of synthesis described there.

The novel compounds of the formula I are in some cases obtained as colorless or pale brown oils, which can be freed from the remaining volatile constituents by prolonged heating to a moderately elevated temperature under reduced pressure (ie. incipient distillation), and can be purified in this manner. If the compounds of the formula I are obtained in a crystalline form, they can be purified by recrystallization.

Since the oximinophosphoric acid derivatives of the formula I can exist in the structurally isomeric syn- and anti-forms, their melting range or boiling range is of little value in characterizing the compounds; hence, they are characterized, in the text below, by the H-NMR spectra and elemental analyses.

The Examples which follow illustrate the preparation of the oximinophosphoric acid derivatives of the formula I.

EXAMPLE 1

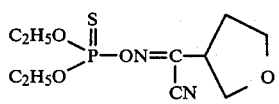

52.8 g of fine sodium hydroxide powder are dissolved in a mixture of 130 ml of water and 400 ml of ethanol. 91.6 g of hydroxylamine hydrochloride in 95 ml of water are added, whilst cooling with ice, the sodium chloride which has precipitated is filtered off, and the filtrate is added dropwise, with vigorous stirring, to 120 g of 3-formyltetrahydrofuran (boiling point 103° C./133 mbar), whilst keeping the temperature below 30° C. The reaction mixture is then stirred for 12 hours at room temperature, after which it is poured into water. The aqueous phase is saturated with sodium chloride and extracted about eight times with 125 ml of ether at a time. The combined extracts are dried over sodium sulfate. The residue which is left on stripping off the solvent is distilled at 0.4 mbar, at which pressure 88 g of 3-formyltetrahydrofuranoxime pass over, as a colorless liquid, at 78°–82° C.; yield: 64% of theory.

$C_5H_9NO_2$ (115)— calculated: C, 52.2; H, 7.9; N, 12.2; found: C, 52.4; H, 8.1; N, 12.3.

60 MHz H-NMR spectrum in $CDCl_3$ (δ values): 1.8–2.65 (2H), 2.8–3.6 (1H), 3.5–4.4 (4H), 6.9 (syn), 7.6 (anti) (1H), 9.1–10.2 (1H).

100 g of chlorine gas are passed into a well-cooled solution of 128 g of 3-formyltetrahydrofuranoxime in 1,400 ml of ether, at below −20° C.; thereafter, all the volatile constituents of the reaction mixture are stripped off in a rotary evaporator at 20° C., the crystalline residue is taken up in 1,000 ml of methylene chloride and the dark blue solution obtained is kept at room temperature until the chloronitroso compound first formed has disappeared. The liquid, which at that stage is colorless, is then added, in the course of three hours, to a suspension, cooled to 10°–15° C., of 79.6 g of potassium cyanide in 800 ml of methanol, after which the batch is stirred for four hours at room temperature. The potassium chloride which has separated out is filtered off, the filtrate is concentrated, the residue is taken up in ethyl acetate and this solution is washed three times with water and is dried over magnesium sulfate. After stripping off the solvent, finally at 0.001 mbar and 40° C., 102.85 g of α-oximino-(tetrahydrofuran-3-yl)-acetonitrile remain in the form of a viscous oil which after a short time solidifies to give a crystalline mass which starts to melt at 28° C.; yield: 66% of theory.

$C_6H_8N_2O_2$ (140)— calculated: C, 51.4; H, 5.8; N, 20.0; found: C, 51.5; H, 5.8; N, 19.7.

100 MHz H-NMR spectrum in $CDCl_3$ (δ values): 2.0–2.5 (2H), 3.1–3.5 (1H), 3.65–4.2 (4H).

7.0 g of α-oximino-(tetrahydrofuran-3-yl)-acetonitrile and 9.43 g of thiophosphoric acid O,O-diethyl ester chloride are introduced into 65 ml of acetone, and 7.25 g of fine potassium carbonate powder are added over two hours, with thorough stirring. The reaction mixture is then stirred for two days at room temperature, after which insoluble constituents are filtered off and the filtrate is concentrated under reduced pressure. The residue is taken up in ether and this solution is washed three times with water, dried over sodium sulfate and freed from solvent. After distilling off the residual volatiles at 0.01 mbar and 50° C., 11.8 g of (O,O-diethylthiophosphoryl)-α-oximino-(tetrahydrofuran-3-yl)-acetonitrile remain, as a virtually colorless, viscous oil; yield: 80% of theory.

$C_{10}H_{17}N_2O_4PS$ (292)— calculated: C, 41.4; H, 5.9; N, 9.5; found: C, 41.5; H, 6.0; N, 9.2.

60 MHz H-NMR spectrum in $CDCl_3$ (δ values): 1.2–1.6 (6H); 2.0–2.5 (2H), 3.05–3.75 (1H), 3.8–4.6 (8H).

EXAMPLE 2

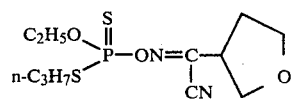

A solution of 7.0 g of α-oximino-(tetrahydrofuran-3-yl)-acetonitrile in 40 ml of absolute tetrahydrofuran is cooled to −40° C. and 31.2 ml of a 1.6-molar solution of n-butyl-lithium in n-hexane are added dropwise. The resulting mixture is warmed to −20° C. in the course of 30 minutes. 10.92 g of dithiophosphoric acid O-ethyl S-n-propyl diester chloride in 20 ml of absolute tetrahydrofuran are then added. After a reaction time of 24 hours at room temperature, the solvent is removed under reduced pressure and the residue is extracted repeatedly with ether. The combined extracts are washed three times with water, dried over sodium sulfate and freed from the solvent. 13.3 g of (O-ethyl S-n-propyl-dithiophosphoryl)-α-oximino-(tetrahydrofuran-3-yl)-acetonitrile are obtained as a yellowish oil; yield: 83% of theory.

$C_{11}H_{19}N_2O_3PS_2$ (322)— calculated: C, 41.0; H, 5.9; N, 8.7; found: C, 41.4; H, 6.3; N, 8.6.

220 MHz H-NMR spectrum in $CDCl_3$ (δ values): 1.0 (3H), 1.35 (3H), 1.6–1.8 (2H), 2.0–2.5 (2H), 2.75–3.1 (3H), 3.5 (1H), 3.6–4.1 (4H), 4.2–4.35 (2H).

EXAMPLE 3

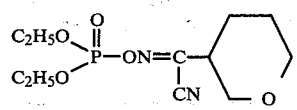

Using a method similar to Example 1, reaction of 114 g of 3-formyltetrahydropyran (boiling point 69° C./18.6 mbar) with 76.4 g of hydroxylamine hydrochloride in the presence of 44 g of sodium hydroxide, followed by working up and distillation, gives 78.6 g of 3-formyltetrahydropyranoxime as a colorless, clear liquid. Boiling point: 85°–87° C./0.13 mbar; yield: 61% of theory.

$C_6H_{11}NO_2$ (129)— calculated: C, 55.8; H, 8.6; N, 10.8; found: C, 56.0; H, 8.4; N, 11.0.

60 MHz H-NMR spectrum in $CDCl_3$ (δ values): 1.1–2.1 (4H), 2.1–2.7 (anti), 2.8–3.4 (syn) (1H), 3.0–4.1 (4H), 6.5 (syn), 7.2 (anti) (1H), 8.9–9.8 (1H).

Using the method described in Example 1, 67 g of 3-formyltetrahydropyranoxime, 40.5 g of chlorine and 37.17 g of potassium cyanide give 73.3 g of α-oximino-(tetrahydropyran-3-yl)-acetonitrile, of melting range 46°–50° C.; yield: 91% of theory.

$C_7H_{10}N_2O_2$ (154)— calculated: C, 54.6; H, 6.6; found: C, 54.9; H, 6.8.

220 MHz H-NMR spectrum in $CDCl_3$ (δ values): 1.4–1.9 (3H), 1.9–2.2 (1H), 2.6–2.8 (1H), 3.3–3.8 (2H), 3.8–4.3 (2H), 10.6–11.4 (1H).

Using the method described in Example 1, 8.47 g of α-oximino-(tetrahydropyran-3-yl)-acetonitrile, 11.36 g of potassium carbonate and 9.96 g of phosphoric acid O,O-diethyl ester chloride give 13.44 g of (O,O-diethylphosphoryl)-α-oximino-(tetrahydropyran-3-yl)-acetonitrile as a virtually colorless, viscous oil; yield: 84% of theory.

$C_{11}H_{19}N_2O_5P$ (290)— calculated: C, 45.5; H, 6.6; N, 9.6; found: C, 45.2; H, 6.8; N, 9.6.

60 MHz H-NMR spectrum in $CDCl_3$ (δ values); 1.3 (6H), 1.4–2.2 (4H), 2.5–3.0 (1H), 3.0–4.5 (6H).

EXAMPLE 4

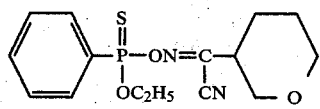

8.83 g of benzene thiophosphonic acid O-ethyl ester chloride are added dropwise to a solution of 6.16 g of α-oximino-(tetrahydropyran-3-yl)-acetonitrile in 60 ml of acetonitrile. 8.24 g of potassium carbonate are introduced in portions, with thorough stirring. After all has been added, the reaction mixture is kept at 40° C. for 12 hours. To work up the mixture, the potassium chloride formed is filtered off, the filtrate is concentrated, the residue is taken up in ethyl acetate and the solution is thoroughly washed with water. It is dried over sodium sulfate, and the residual solvent is removed, finally at 0.07 mbar and 30° C. 12.4 g of (O-ethyl-benzenethiophosphonyl)-α-oximino-(tetrahydropyran-3-yl)-acetonitrile remain; yield: 92% of theory.

$C_{15}H_{19}N_2O_3PS$ (338)—calculated: C, 53.3; H, 5.7; N, 8.2; found: C, 53.2; H, 5.7; N, 7.9.

60 MHz H-NMR spectrum in $CDCl_3$ (δ values); 1.45 (3H), 1.3–2.4, 2.5–3.1 (1H), 3.2–4.85 (6H), 7.5–7.9 (3H), 7.9–8.5 (2H).

EXAMPLE 5

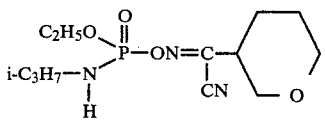

Using a method similar to Example 4, reaction of 7.7 g of α-oximino-(tetrahydropyran-3-yl)-acetonitrile with 9.27 g of phosphoric acid ethyl ester N-isopropylamide chloride in the presence of 10.3 g of potassium carbonate gives 13.1 g of (O-ethyl N-isopropylamidephosphoryl)-α-oximino-(tetrahydropyran-3-yl)-acetonitrile.

$C_{12}H_{22}N_3O_4P$ (303)—calculated: C, 47.5; H, 7.3; N, 13.8; found: C, 47.7; H, 7.4; N, 13.5.

80 MHz H-NMR spectrum in $CDCl_3$ (δ values): 1.1–1.3 (6H), 1.3–1.55 (3H), 1.6–2.3 (5H), 2.5–3.0 (1H), 3.1–4.0 (5H), 3.9–4.3 (2H).

EXAMPLE 6

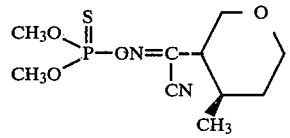

Using the procedure described in Example 1, 76.4 g of hydroxylamine hydrochloride, 44 g of sodium hydroxide and 128 g of 4-methyl-3-formyl-tetrahydropyran (boiling point 72° C./17.3 mbar) give 123 g of the corresponding aldoxime, boiling at 89°–95° C./0.13 mbar; yield: 86% of theory.

$C_7H_{13}NO_2$ (143)—calculated: C, 58.7; H, 9.2; N, 9.8; found: C, 58.5; H, 9.0; N, 10.1.

60 MHz H-NMR spectrum in $CDCl_3$ (δ values): 0.8–1.1 (3H), 1.2–1.8 (3H), 1.9–2.5 (1H), 2.9–3.6 (2H), 3.7–4.2 (2H), 6.4 (syn), 7.2 (anti) (1H), 8.7–9.9 (1H).

Using a method of synthesis similar to that described in Example 1, 71.5 g of 4-methyl-3-formyltetrahydropyranoxime are reacted first with 39.05 g of chlorine and then with 35.81 g of potassium cyanide. 68.8 g of α-oximino-(4-methyl-tetrahydropyran-3-yl)-acetonitrile, melting at 94°–96° C., are obtained; yield: 77% of theory.

$C_8H_{12}N_2O_2$ (169)—calculated: C, 56.9; H, 7.2; N, 16.6; found: C, 56.9; H, 7.2; N, 16.3.

60 MHz H-NMR spectrum in $CDCl_3$ ($\delta$ values): 0.9–1.3 (3H), 1.3–2.2 (3H), 2.2–2.9 (1H), 3.3–3.9 (2H), 3.9–4.4 (2H), 10.0–10.9 (1H).

Reaction of 8.45 g of this oxime with 8.25 g of thiophosphoric acid O,O-dimethyl ester chloride in the presence of 10.32 g of potassium carbonate gives 13.93 g of (O,O-dimethylthiophosphoryl)-α-oximino-(4-methyltetrahydropyran-3-yl)-acetonitrile as a yellowish oil.

$C_{10}H_{17}N_2O_4PS$ (292)—calculated: C, 41.1; H, 5.9; N, 9.5; found: C, 41.2; H, 6.1; N, 9.2.

60 MHz H-NMR spectrum in $CDCl_3$ ($\delta$ values): 1.0 (3H), 1.2–2.2 (3H), 2.25–2.7 (1H), 3.0–4.1 (4H), 3.7 (6H).

EXAMPLE 7

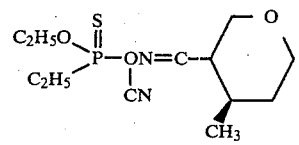

Using a method similar to Example 6, 8.4 g of α-oximino-(4-methyltetrahydropyran-3-yl)-acetonitrile are reacted with 8.62 g of ethane thiophosphonic acid O-ethyl ester chloride and 10.3 g of potassium carbonate; 14.2 g of (O-ethyl-ethanethiophosphonyl)-α-oximino-(4-methyltetrahydropyran-3-yl)-acetonitrile are obtained; yield: 93% of theory.

$C_{12}H_{21}N_2O_3PS$ (304)—calculated: C, 47.4; H, 6.9; N, 9.2; found: C, 47.7; H, 7.1; N, 9.3;

80 MHz H-NMR spectrum in $CDCl_3$ ($\delta$ values): 0.9–1.5 (9H), 1.5–2.7 (7H), 3.2–4.4 (6H).

The following are examples of other compounds of the formula I which may be prepared by a similar method:

| No. | $R^1$ | $R^2$ | $R^3$ | X | n | H-NMR data (MHz, solvent, $\delta$ values) |
|---|---|---|---|---|---|---|
| 8 | $CH_3$ | $CH_3O$ | $CH_3$ | O | 2 | (60, $CDCl_3$) 1.0(3H), 1.2–2.2(3H), 2.25–2.7(1H), 3.05–4.1(4H), 3.6(6H) |
| 9 | $C_2H_5$ | $C_2H_5O$ | $CH_3$ | O | 2 | (100, $CDCl_3$) 1.0(3H), 1.35(6H), 1.4–2.15(3H), 2–2.7(1H), 3.2–3.6(2H), 3.8–4.15(2H), 4.05–4.4(4H) |
| 10 | $C_2H_5$ | $C_2H_5O$ | $CH_3$ | S | 2 | (60, $CDCl_3$) 1.05(3H), 1.35(6H), 1.4–2.1(3H), 2.3–2.8(1H), 3.2–3.7(2H), 3.75–4.6(6H) |
| 11 | $C_2H_5$ | $S-i-C_4H_9$ | $CH_3$ | S | 2 | (60, $CDCl_3$), 0.8–2.2(17H), 2.3–2.85(1H), 3.1–3.7(3H), 3.7–4.6(4H) |
| 12 | $C_2H_5$ | $S-n-C_3H_7$ | $CH_3$ | S | 2 | (60, $CDCl_3$) 0.8–1.2(6H), 1.3–2.1(5H), 1.4(3H), 2.4–3.8(5H), 3.8–4.6(4H) |
| 13 | $C_2H_5$ | $O-C_2H_5$ | H | S | 2 | (220, $CDCl_3$) 1.3(6H), 1.6–1.8(3H), 2.0–2.2(1H), 3.3–3.7(2H), 3.9(1H), 4.05(1H), 4.1–4.4(4H) |
| 14 | $CH_3$ | $CH_3O$ | H | O | 2 | (220, $CDCl_3$) 1.6–2.0(3H), 2.05–2.3(1H), 2.8–3.1(1H), 3.4–3.7(2H), 3.95(6H), 4.0–4.2(1H) |
| 15 | $C_2H_5$ | $S-i-C_4H_9$ | H | S | 2 | (60, $CDCl_3$) 0.9–1.2(3H), 1.3–1.6(6H), 1.5–2.3(6H), 2.6–3.1(1H), 3.2–4.6(7H) |
| 16 | $CH_3$ | $OCH_3$ | H | S | 2 | (60, $CDCl_3$) 1.5–2.4(4H), 2.5–3.2(1H), 3.2–4.3(4H), 3.9(6H) |
| 17 | $C_2H_5$ | $CH_3$ | H | S | 2 | (60, $CDCl_3$) 1.3(3H), 1.4–2.2(4H), 2.95(3H), 2.55–3.15(1H), 3.1–4.1(6H) |
| 18 | $C_2H_5$ | $S-n-C_3H_7$ | H | S | 2 | (60, $CDCl_3$) 1.0(3H), 1.4(3H), 1.5–2.2(6H), 2.5–3.2(3H), 3.2–4.5(4H) |
| 19 | $C_2H_5$ | $C_6H_5$ | S | S | 2 | (60, $CDCl_3$) 0.95(3H), 1.1–2.2(6H), 2.3–2.85(1H), 3.2–3.8(2H), 3.85–4.3(2H), 4.3–4.48(2H), 7.4–8.5(5H) |
| 20 | $C_2H_5$ | $S-n-C_3H_7$ | $CH_3$ | O | 2 | (60, $CDCl_3$) 0.9–1.3(6H), 1.3–2.3(5H), 1.45(3H), 2.5–3.9(5H), 3.9–4.7(4H) |
| 21 | $C_2H_5$ | $NH_2$ | $CH_3$ | O | 2 | (80, $CDCl_3$) 1.0(3H), 1.3–1.5(3H), 1.5–2.2(4H), 2.3–2.7(1H), 3.1–3.6(3H), 3.6–4.3(4H) |
| 22 | $C_2H_5$ | $S-n-C_3H_7$ | H | O | 2 | (100, $CDCl_3$) 1.0(3H), 1.35(3H), 1.5–2.2(6H), 2.6–3.1(3H), 3.2–4.45(6H) |
| 23 | $CH_3$ | $C_2H_5$ | $CH_3$ | S | 2 | (80, $CDCl_3$) 0.9–1.5(6H), 1.5–1.9(3H), 1.9–2.35(2H), 2.35–2.7(1H), 3.2–4.0(4H), 3.7(3H) |
| 24 | $CH_3$ | $C_2H_5$ | H | S | 2 | (100, $CDCl_3$) 1.0–1.5(3H), 1.5–1.4(4H), 1.9–2.4(2H), 2.7–3.0(1H), 3.3–4.2(4H), 3.75(3H) |
| 25 | $C_2H_5$ | $C_2H_5$ | H | S | 2 | (80, $CDCl_3$) 0.9–1.5(6H), 1.5–2.0(4H), 1.9–2.4(2H), 2.6–2.95(1H), 3.2–4.4(6H) |
| 26 | $C_2H_5$ | $NH-i-C_3H_7$ | $CH_3$ | O | 2 | (80, $CDCl_3$) 0.9–1.15(3H), 1.1–1.3(6H), |

-continued $$R^1O \underset{R^2}{\overset{X}{\underset{\|}{P}}}-ON=C-\underset{CN}{\overset{R^3}{\underset{|}{C}}}\overset{(CH_2)_n}{\underset{O}{\diagdown}}$$

| No. | $R^1$ | $R^2$ | $R^3$ | X | n | H-NMR data (MHz, solvent, δ values) |
|---|---|---|---|---|---|---|
| | | | | | | 1.3–1.5(3H), 1.5–2.2(4H), 2.3–2.7(1H), 3.1–3.6(2H), 3.6–4.3(4H) |
| 27 | $C_2H_5$ | $N(CH_3)_2$ | $CH_3$ | O | 2 | (80, $CDCl_3$) 1.0(3H), 1.35(3H), 1.5–2.1(3H), 2.3–2.8(1H), 2.65(6H), 3.1–3.6(2H), 3.7–4.3(4H) |
| 28 | $C_2H_5$ | $N(CH_3)_2$ | H | O | 2 | (80, $CDCl_3$) 1.2–1.5(3H), 1.5–2.3(4H), 2.5–3.0(1H), 2.65(6H), 3.2–3.85(5H), 3.9–4.3(2H) |
| 29 | $C_2H_5$ | $C_2H_5$ | H | S | 1 | (220, $CDCl_3$) 1.05–1.55(6H), 2.05–2.6(4H), 3.4–3.6(1H), 3.7–4.2(4H), 4.2–4.45(2H) |
| 30 | $CH_3$ | $OCH_3$ | H | S | 1 | (60, $CDCl_3$) 1.2–1.55(3H), 1.8–2.65(5H), 3.2–3.7(1H), 3.7–4.8(6H) |
| 31 | $C_2H_5$ | $CH_3$ | H | S | 1 | (60, $CDCl_3$) 1.2–1.55(3H), 1.8–2.65(5H), 3.2–3.7(1H), 3.7–4.8(6H) |
| 32 | $CH_3$ | $C_2H_5$ | H | S | 1 | (60, $CDCl_3$) 0.9–1.7(3H), 1.9–2.65(4H), 3.25–4.4(8H) |
| 33 | $C_2H_5$ | $S-i-C_4H_9$ | H | S | 1 | (60, $CDCl_3$) 0.85–1.25(3H), 0.85–2.5 (10H), 3.2–4.7(8H) |
| 34 | $CH_3$ | $OCH_3$ | H | O | 1 | (80, $CDCl_3$) 2.0–2.55(2H), 3.2–3.6(1H), 3.7–4.6(10H) |
| 35 | $C_2H_5$ | $OC_2H_5$ | H | O | 1 | (80, $CDCl_3$) 1.35(6H), 2.0–2.5(2H), 3.2–3.6(1H), 3.7–4.45(8H) |

The oximinophosphoric acid derivatives of the formula I according to the invention are suitable for effectively combating pests from the class of insects, ticks, mites and nematodes. They may be used for crop protection, and in the hygiene, stores protection and veterinary sectors.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monocha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aeygpti, Aedes vexans, Tabanus bovinus, Musca domestica, Fannia canicularis, Muscina stabulans, Glossina morsitans, Oestrus ocis, Chrysomya macellaria, Chrysomya hominivorax, Lucilia cuprina, Lucilia sericata* and *Hypoderma lineata;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasis, Dysaulacorthum pseudosolani, Acyrthosiphon onobrychis, Marcosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes* and *Termes natalensis;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum,*

*Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Paratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethylsulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyester alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below:

I. 3 parts by weight of active ingredient no. 1 is intimately mixed with 97 parts by weight of particulate kaolin. A dust is obtained containing 3% by weight of the active ingredient.

II. 30 parts by weight of active ingredient no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of active ingredient no. 7 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

IV. 20 parts by weight of active ingredient no. 30 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formations contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing more than 95 wt% of active ingredient, or even the 100% active ingredient.

There may be added to the individual active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butyl-phenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenyl-phosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)fluorophosphine oxide, octamethyl-pyrophosphoramide, O,O,O,O-tetraethyldithiopyrophosphate, S-chloromethyl-O,O-diethylphosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, α-hexachlorocyclohexane, 1,1-di-(p-methoxyphenyl)- 2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, α-cyano-3-phenoxybenzyl(±)-cis,trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and α-cyano-3-phenoxybenzyl-α-isopropyl-4-chlorophenylacetate.

The following examples illustrate the biological action of the novel compounds. The agents used for comparison purposes were the prior art active ingredients O,O-diethyl-S-(2-chloro-1-phthalimidoethyl)-phosphorodithioate (German Published Application DAS No. 1,545,977), O,O-diethylacetone oxime thiophosphate (German Published Application DAS No. 1,052,981), O,O-dimethylthionophosphoryl-α-oximino-2-methylphenylacetic acid nitrile (German Published Application DAS No. 1,238,902) and O,O-dimethyl-(1-cyano-1-cyclohexyl)ketone oxime thionophosphoric acid ester (German Laid-Open Application DOS No. 2,304,848).

The active ingredients are numbered as in the foregoing examples and tables.

EXAMPLE A

Contact action on red flour beetles (*Tribolium castaneum*) resistant to malathion Red flour beetles are placed inside glass rings having a diameter of 4.5 cm on circular filter papers (diameter: 0.7 cm) treated with acetonic solutions of the active ingredients.

The kill rate is determined after 24 hours. Active ingredients nos. 1, 6, 7, 8, 9, 10, 13, 14, 16, 17, 29, 30, 31 and 32 proved to have an action greatly superior to that of the prior art active ingredients.

EXAMPLE B

Contact action on granary weevils (*Sitophilus granarius*)

Petri dishes 10 cm in diameter are lined with acetonic solutions of the active ingredients. After the solvent has evaporated, 100 granary weevils are placed in each dish.

After 4 hours, the weevils are transferred to untreated vessels. The kill rate is determined after 24 hours, by counting how many weevils are, after this period has elapsed, capable of leaving an untreated cardboard dish (40 mm in diameter, 10 mm high) within 60 minutes.

The kill rate for weevils exposed to active ingredients nos. 3, 6, 7, 8, 9, 10, 13, 14, 16 and 17 is, at the same amount of compound per dish, much higher than than for weevils exposed to the prior art active ingredients.

EXAMPLE C

Contact action on cockroaches (*Blatta orientalis*)

The bottom of 1-liter preserving jars is treated with acetonic solutions of the active ingredients. After the solvent has evaporated, 5 adult cockroaches are placed in each jar, and the kill rate is determined after 48 hours.

In this test, active ingredients nos. 3, 6, 7, 8, 9, 10, 13, 15, 16 and 17 had a better action than the prior art compounds.

EXAMPLE D

Contact action on houseflies (*Musca domestica*)

1 μl of the active ingredients dissolved in acetone is administered by means of a microsyringe to the ventral abdomen of 4-day old imagoes under slight $CO_2$ narcosis.

20 animals treated in the same way are then placed in a plastic bag having a volume of approx. 500 ml. After 4 hours, the animals in supine position are counted and the $LD_{50}$ is worked out by means of a graph.

The $LD_{50}$ of active ingredients nos. 3, 7, 8, 13, 16, 17 and 23 is lower than that of the prior art compounds.

EXAMPLE E

Contact action on bean aphids (*Aphis fabae*); spray experiment

Potted bean plants (*Vicia faba*) with extensive bean aphid colonies are sprayed to runoff in a spray booth with aqueous formulations of the active ingredients. The action is assessed after 48 hours.

A kill rate of 100% was achieved with much lower amounts of active ingredients nos. 3, 5, 6, 7, 11, 13, 14, 15, 16, 17, 23, 26 and 27 than the amounts of the prior art compounds necessary to achieve 100% kill.

EXAMPLE F

Contact action on cotton stainers (*Dysdercus intermedius*)

Petri dishes 10 cm in diameter are lined with 1 ml of acetonic solutions of the active ingredients.

After the solvent has evaporated, 20 larvae in the penultimate stage are placed in each dish and the action is registered after 24 hours.

Active ingredients nos. 3, 6, 8, 9, 10, 13, 14, 16, 17 and 22 had a better action than the comparative compounds.

EXAMPLE G

Contact action on ticks (*Ornithodorus moubata*)

Ticks in the 3rd larval stage are placed in paper bags and dipped for 3 seconds in the emulsion under investigation. The bags are then suspended. The action on the ticks is assessed after 48 hours.

In this test, a kill rate of 100% is achieved with emulsion concentrations of active ingredients nos. 3, 5, 7, 9, 10, 13, 14 and 17 much lower than those of the prior art compounds.

EXAMPLE H

Action on root-knot nematodes (*Meloidogyne incognita*)

The experiments are carried out with 500 g of compost heavily infested with root-knot nematodes. Treatment with the aqueous active ingredient formulations is effected by pouring 20 ml of formulation onto the soil.

After 6 to 8 weeks root-knot formation is assessed. Formulations containing 0.1% of active ingredients nos. 3, 10 and 11 prevented root-knot formation.

We claim:

1. An oximinophosphoric acid derivative of the formula $$\begin{array}{c} R^1O \\ \diagdown \\ R^2 \end{array} \overset{X}{\underset{\parallel}{P}} -O-N=C- \overset{R^3}{\underset{|}{\overset{|}{\bigcirc}}} \overset{(CH_2)_n}{\underset{O}{\bigcirc}}, \quad (I)$$

where $R^1$ is unbranched or branched alkyl of up to 4 carbon atoms, $R^2$ is unbranched or branched alkoxy or alkylthio of up to 4 carbon atoms, unbranched or branched alkyl of up to 3 carbon atoms, phenyl, amino, alkylamino or dialkylamino, where each alkyl is unbranched or branched and of up to 4 carbon atoms, $R^3$ is hydrogen or methyl, X is oxygen or sulfur and n is 1 or 2.

2. (O,O-diethylthiophosphoryl)-α-oximino-tetrahydropyran-3-yl-acetonitrile.

3. The compound of the formula $$\begin{array}{c} CH_2H_5O \\ \diagdown \\ CH_3 \end{array} \overset{S}{\underset{\parallel}{P}} -O-N=C- \overset{|}{\underset{CN}{\bigcirc}} \overset{\bigcirc}{\underset{O}{\bigcirc}}$$

4. A pesticide comprising solid and/or liquid additives and a pesticidally effective amount of an oximinophosphoric acid derivative of the formula I as claimed in claim 1.

5. A process for combating pests, wherein a pesticidally effective amount of an oximinophosphoric acid derivative of the formula I as claimed in claim 1 is allowed to act on pests or their habitat.

* * * * *